(12) United States Patent
Nielsen

(10) Patent No.: US 9,644,492 B2
(45) Date of Patent: May 9, 2017

(54) DE-LAMINATION INDICATOR

(71) Applicant: Siemens Aktiengesellschaft, Munich (DE)

(72) Inventor: Soeren E. Nielsen, Skanderborg (DK)

(73) Assignee: Siemens Aktiengesellschaft, Munich (DE)

( * ) Notice: Subject to any disclaimer, the term of this patent is extended or adjusted under 35 U.S.C. 154(b) by 22 days.

(21) Appl. No.: 14/585,597

(22) Filed: Dec. 30, 2014

(65) Prior Publication Data

US 2015/0204209 A1    Jul. 23, 2015

(30) Foreign Application Priority Data

Jan. 20, 2014   (EP) .................................... 14151790

(51) Int. Cl.

| | |
|---|---|
| *G01R 33/09* | (2006.01) |
| *G01R 31/26* | (2014.01) |
| *F01D 21/00* | (2006.01) |
| *G01N 27/20* | (2006.01) |
| *F01D 5/28* | (2006.01) |
| *G01M 15/14* | (2006.01) |

(Continued)

(52) U.S. Cl.
CPC ........... *F01D 21/003* (2013.01); *F01D 5/282* (2013.01); *F03D 17/00* (2016.05); *G01M 15/14* (2013.01); *G01N 27/20* (2013.01); *G01R 31/025* (2013.01); *F05B 2270/821* (2013.01); *Y02E 10/721* (2013.01); *Y10T 29/49316* (2015.01)

(58) Field of Classification Search
CPC .... G01R 33/09; G01R 33/098; G01R 33/093; H01L 2924/00; H01L 2924/0002; H01L 22/32

USPC .... 324/252, 538, 762.01, 762.05, 719, 71.5, 324/765, 760.02, 760.01, 537, 500, 555, 324/718, 456, 237, 238, 240, 713; 257/48, E21.522, E23.179, E21.525, 257/E21.523; 348/125, 246, 247, 615; 702/35; 73/615

See application file for complete search history.

(56) References Cited

U.S. PATENT DOCUMENTS

| | | | |
|---|---|---|---|
| 2001/0006215 A1* | 7/2001 | Cowan ................. | G01N 23/046 250/393 |
| 2006/0017540 A1* | 1/2006 | Smith .................... | H01H 85/32 337/242 |

(Continued)

*Primary Examiner* — Melissa Koval
*Assistant Examiner* — Taqi Nasir
(74) *Attorney, Agent, or Firm* — Beusse Wolter Sanks & Maire

(57) ABSTRACT

An indicator device for detecting a delamination of a composite material, including detecting a delamination of a composite material of a wind turbine or a wind turbine rotor blade is provided. The indicator device includes: A first part, a second part and an electric circuit. Therein, the first part comprises at least a part of a lower part of the electric circuit. The second part comprises at least a part of an upper part of the electric circuit. And the lower part and the upper part are electrically connected to each other at a predetermined breaking point forming the electric circuit in such a manner, that when the indicator device is in use in a composite material, if a delamination of the respective composite material occurs, the electric connection between the lower part and the upper part breaks at the predetermined breaking point, thus cutting the electric circuit.

18 Claims, 1 Drawing Sheet

(51) Int. Cl.
*G01R 31/02* (2006.01)
*F03D 17/00* (2016.01)

(56) References Cited

U.S. PATENT DOCUMENTS

| | | | |
|---|---|---|---|
| 2009/0035131 A1* | 2/2009 | McMillan | F04D 29/668 415/200 |
| 2009/0201043 A1* | 8/2009 | Kaltalioglu | G01R 31/2858 324/750.3 |
| 2009/0246892 A1* | 10/2009 | Maloney | H01L 22/34 438/15 |
| 2010/0171518 A1 | 7/2010 | Picot | |
| 2011/0298485 A1* | 12/2011 | Narazaki | G01R 31/026 324/755.05 |
| 2013/0170991 A1* | 7/2013 | Olesen | B29C 65/4835 416/61 |
| 2014/0072440 A1* | 3/2014 | Jacobsen | F03D 1/06 416/241 R |

* cited by examiner

DE-LAMINATION INDICATOR

CROSS REFERENCE TO RELATED APPLICATIONS

This application claims the benefit of European Application No. EP14151790 filed Jan. 20, 2014, incorporated by reference herein in its entirety.

FIELD OF INVENTION

The present invention relates to the field of wind turbines.

ART BACKGROUND

Wind turbine blades may consist of laminate material. If a de-lamination of a wind turbine blade occurs, this may lead to larger damages to the rotor blade or may even lead to hazards of dropping the blade.

Hence, there may be a need to provide an early warning system for a detection of a delamination of laminated parts of a wind turbine.

SUMMARY OF THE INVENTION

This need may be met by the subject matter according to the independent claims. Advantageous embodiments of the present invention are described by the dependent claims.

According to a first aspect of the invention there is provided an indicator device for detecting a delamination of a composite material, including for detecting a delamination of a composite material of a wind turbine, or for detecting a delamination of a composite material of a wind turbine rotor blade. Therein, the indicator device comprises: A first part, a second part and an electric circuit. The first part comprises at least a part of a lower part of the electric circuit. The second part comprises at least a part of an upper part of the electric circuit. And the lower part and the upper part are electrically connected to each other at a predetermined breaking point forming the electric circuit in such a manner, that when the indicator device is in use in a composite material, if a delamination of the respective composite material occurs, the electric connection between the lower part and the upper part breaks at the predetermined breaking point, thus cutting the electric circuit.

The advantage of this concept is that a de-lamination of a composite material may be detected at the time the de-lamination occurs. With this, a further de-lamination of this composite material may be prevented, which therefore may prevent a respective wind turbine from a severe damage.

This aspect of the invention is based on the idea that by using an respective indicator in a composite material, a first de-lamination of a de-lamination process may be detected, and therefore a further de-lamination of the respective composite material may be prevented, for example by exchanging the respective de-laminated unit.

According to a further embodiment of the invention the lower part of the electric circuit is fixed to a bottom part of the first part.

This embodiment of the invention is based on the idea that by fixing the lower part of the electric circuit to a bottom part of a first layer of a composite material, an offset of two composite material layers to each other may be detected.

According to a further embodiment of the invention the second part comprises an electrical connection of the electric circuit, wherein the electrical connection is adapted for being connected to an external monitoring system.

This embodiment of the invention is based on the idea that by providing an electrical connection to the external of the composite material, a monitoring of the composite material may be provided. Therefore, if a de-lamination is detected, the monitoring may allow for a quick reaction to prevent a further de-lamination of the composite material, for instance by turning-off the respective wind turbine.

According to a further embodiment of the invention the electric circuit acts a shunt.

This embodiment of the invention is based on the idea that by providing a shunt acting as the electric circuit, an easy way of monitoring the respective composite material may be provided.

According to a further embodiment of the invention when the indicator device is in use in the composite material, if a displacement of two layers of the respective monitored composite material relative to each other occurs, the electric connection between the lower part and the upper part breaks at the predetermined breaking point, thus cutting the electric circuit.

This embodiment of the invention is based on the idea that by providing a predetermined breaking point in the indicator device, it may be ensured that the electric circuit may respond to an offset of respective layers of the composite material to each other in a certain way.

According to a further embodiment of the invention the displacement is caused by a shear stress in a parallel plane to a boundary plane between the respective two layers of the respective composite material.

This embodiment of the invention is based on the idea that a displacement may occur by an offset of respective layers of the composite material to each other, caused by shear stress.

According to a further embodiment of the invention the displacement is caused due at least a partial separation of the respective two layers of the respective composite material.

This embodiment of the invention is based on the idea that a displacement may occur, caused by a lifting of one respective layer of the composite material from another layer of the composite material.

According to a further embodiment of the invention the electric connection between the lower part and the upper part breaks at the predetermined breaking point at a displacement of at least 1 mm, and advantageously at a displacement of at least 0.1 mm.

This embodiment of the invention is based on the idea that by enabling the electric connection to break at the predetermined breaking point at a displacement of at least 1 mm, and advantageously of at least 0.1 mm, a very small de-lamination may be detected.

According to a second aspect of the invention there is provided a delamination detecting system for detecting a delamination of a composite material, including for detecting a delamination of a composite material of a wind turbine, or for detecting a delamination of a composite material of a wind turbine rotor blade. Therein, the delamination detecting system comprises: The composite material and at least one indicator device according to any one of the embodiments of the first aspect of the invention. Therein, the composite material comprises a bottom layer and a top layer. A lower part of each indicator device is fixed in the bottom layer. An upper part of each indicator device is fixed on a surface of the top layer. And the surface of the top layer is facing away from the bottom layer.

This aspect of the invention is based on the idea that by providing a composite material, which already integrates an indicator device according to the invention, an easy way of detecting a de-lamination in a respective unit may be provided, which may reduce cost of production of the respective unit.

According to a further embodiment of the invention the delamination detecting system comprises a plurality of indicator devices according to any one of the embodiments of the first aspect of the invention. Therein, the plurality of indicator devices is arranged in the composite material in such a manner, that an area of delamination of the composite material may be localized.

This embodiment of the invention is based on the idea that by arranging the plurality of indicators in a certain way, the location of de-lamination of the respective composite material may be narrowed down.

According to a third aspect of the invention there is provided a wind turbine rotor blade comprising a delamination detecting system of any one of the embodiments of the second aspect of the invention.

This aspect of the invention is based on the idea that by providing a wind turbine rotor blade with a respective delamination system even existing wind turbines may be upgraded with a respective rotor blade according to this aspect of the invention.

According to a fourth aspect of the invention there is provided a wind turbine comprising a wind turbine rotor blade of any one of the embodiments of the third aspect of the invention.

This aspect of the invention is based on the idea that by providing a wind turbine comprising a wind turbine rotor blade according to third aspect of the invention, wind turbines may be protected against sever damages, which may otherwise occur by a progressing and undetected de-lamination process of a respective composite material in a conventional wind turbine rotor blade.

According to a fifth aspect of the invention there is provided a method for manufacturing a delamination detecting system, including a delamination detecting system for a wind turbine, or a delamination detecting system for a wind turbine rotor blade, the method comprising:—Inserting at least one indicator device according to any embodiment of the first aspect of the invention into a respective hole of the composite material.—Fixedly arranging at least a part of a first part of each indicator device in a bottom layer of the composite material, including by gluing.—Fixedly arranging at least a part of a second part of each indicator device on a surface of a top layer of the composite material, including by gluing, wherein the surface is facing away from the bottom layer of the composite material.

This aspect of the invention is based on the idea that by providing a method according to this aspect of the invention, a possibility of assembling a respective delamination detecting system is provided.

It has to be noted that embodiments of the invention have been described with reference to different subject matters. In particular, some embodiments have been described with reference to method type claims whereas other embodiments have been described with reference to apparatus type claims. However, a person skilled in the art will gather from the above and the following description that, unless other notified, in addition to any combination of features belonging to one type of subject matter also any combination between features relating to different subject matters, in particular between features of the method type claims and features of the apparatus type claims is considered as to be disclosed with this document.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
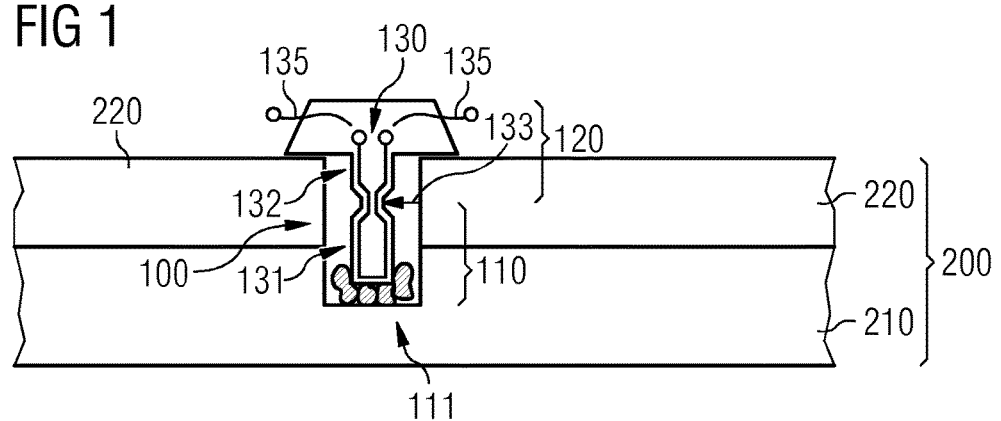
FIG. 1 shows a schematically drawing of a proposed indicator device for detecting a delamination of a composite material according to an exemplary embodiment of the invention.

The illustration in the drawing is schematically. It is noted that in different figures, similar or identical elements or features are provided with the same reference signs or with reference signs, which are different from the corresponding reference signs only within the first digit. In order to avoid unnecessary repetitions elements or features which have already been elucidated with respect to a previously described embodiment are not elucidated again at a later position of the description.

FIG. 1 shows a schematically drawing of a proposed indicator device for detecting a delamination of a composite material according to an exemplary embodiment of the invention.

In FIG. 1 is shown an indicator device 100 for detecting a delamination of a composite material 200, including for detecting a delamination of a composite material 200 of a wind turbine, or for detecting a delamination of a composite material 200 of a wind turbine rotor blade, the indicator device 100 comprises: A first part 110, a second part 120 and an electric circuit 130. Therein, the first part 110 comprises at least a part of a lower part 131 of the electric circuit 130. The second part 120 comprises at least a part of an upper part 132 of the electric circuit 130. And the lower part 131 and the upper part 132 are electrically connected to each other at a predetermined breaking point 133 forming the electric circuit 130 in such a manner, that when the indicator device 100 is in use in a composite 200 material, if a delamination of the respective composite material 200 occurs, the electric connection between the lower part 131 and the upper part 132 breaks at the predetermined breaking point 133, thus cutting the electric circuit 130.

Moreover, the lower part 131 of the electric circuit 130 is fixed to a bottom part 111 of the first part 110. Moreover, the upper part 132 of the electric circuit 130 is fixed inside the second part 120. The second part 120 further comprises an electrical connection 135 of the electric circuit 130, wherein the electrical connection 135 is adapted for being connected to an external monitoring system. Moreover, the electric circuit 130 acts a shunt. Moreover, when the indicator device 100 is in use in the composite 200 material, if a displacement of two layers 210, 220 of the respective monitored composite material 200 relative to each other occurs, the electric connection between the lower part 131 and the upper part 132 breaks at the predetermined breaking point 133, thus cutting the electric circuit 130.

The indicator device 100 may be installed for example in a 6 mm hole, which may be drilled in the composite material 200. For the example of a root of a wind turbine, the depth of the hole could penetrate both an outer surface laminate as a top layer 220 and an inner root segment as a bottom layer 210.

The indicator device 100 may be installed in the hole and the inner distal part of the indicator device 100, which may be seen as at least a part of a first part 110 of the indicator device 100, may be glued to the inner root segment 210, whereas the outer distal part of the indicator device 100, which may be seen as at least a part of a second part 120 of the indicator device 100, may be established/glued to the said outer surface laminate 220.

The indicator device 100 may comprise for example a simple wire-loop, which act as an electrical circuit 130. The two wire ends may act as an electrical connection 135 of the electric circuit 130 and may be terminated on the outer distal part of the indicator 120 and may be prepared to be connected to some external measuring electrical indicator system, which may act as a monitoring system.

Under normal conditions, the said wire-loop 130 may conduct an applied current and act as a shunt.

Under de-lamination conditions where for example the said inner root segment 210 and said outer surface laminate 220 displace relative to each other due to shear stress, the said inner distal part 110 of the indicator device 100, which is fixed relative to the root segment 210, is also displaced relative to said outer distal part 120 of the indicator device 100. This in turn breaks the wire-loop 130 and thus the electric circuit 130 of the indicator device 100 is cut. The sensitivity for the indicator device may for one example be so that the wire-loop 130 breaks at a shear displacement of for example 1 mm.

The indicator device may also be constructed so that it can react to displacements due to separation of the composite layers 210, 220, for example due to a so called peel-effect. The sensitivity for the indicator device 100 may for one example be so that the wire breaks at a separation displacement of for example 0.1 mm.

Figure 2:
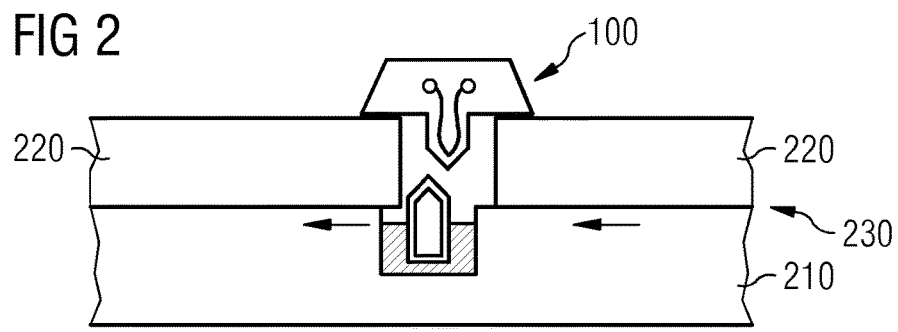
FIG. 2 shows a schematically drawing of a proposed indicator device for detecting a delamination of a composite material, if a displacement is caused by a shear stress in a parallel plane to a boundary plane between two layers of a composite material according to an exemplary embodiment of the invention.

FIG. 2 shows a schematically drawing of a proposed indicator device for detecting a delamination of a composite material, if a displacement is caused by a shear stress in a parallel plane to a boundary plane between two layers of a composite material according to an exemplary embodiment of the invention.

In FIG. 2 the displacement is caused by a shear stress in a parallel plane to a boundary plane 230 between the respective two layers 210, 220 of the respective composite material 200. As a result, the electric connection between the lower part 131 and the upper part 132 breaks at the predetermined breaking point 133, thus cutting the electric circuit 130, which indicates that a de-lamination occurred.

Figure 3:
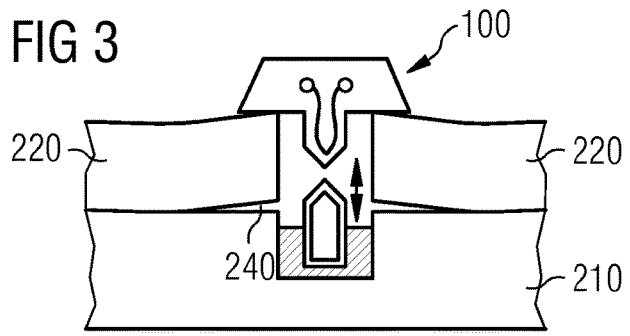
FIG. 3 shows a schematically drawing of a proposed indicator device for detecting a delamination of a composite material, if a displacement is caused due at least a partial separation of two layers of a composite material according to an exemplary embodiment of the invention.

FIG. 3 shows a schematically drawing of a proposed indicator device for detecting a delamination of a composite material, if a displacement is caused due at least a partial separation of two layers of a composite material according to an exemplary embodiment of the invention.

In FIG. 3 the displacement is caused due at least a partial separation 240 of the respective two layers 210, 220 of the respective composite material 200. As a result, again, the electric connection between the lower part 131 and the upper part 132 breaks at the predetermined breaking point 133, thus cutting the electric circuit 130, which indicates that a delamination occurred.

Figure 4:
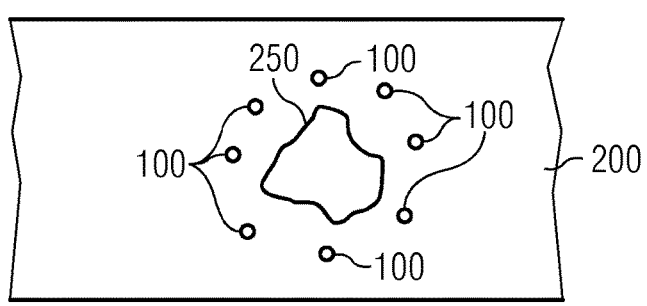
FIG. 4 shows a schematically drawing of a proposed delamination detecting system for localizing an area of delamination of a composite material according to an exemplary embodiment of the invention.

FIG. 4 shows a schematically drawing of a proposed delamination detecting system for localizing an area of delamination of a composite material according to an exemplary embodiment of the invention.

In FIG. 4 is shown a delamination detecting system comprising a plurality of indicator devices 100 according to an embodiment of the invention. Therein, the plurality of indicator devices 100 is arranged in the composite material 200 in such a manner, that an area of delamination 250 of the composite material 200 may be localized.

For one example, if an area of delamination 250 in a composite material 200 may be already known, one or more indicators devices 100 may be established in the surrounding composite structure, in order to monitor if the area of delamination 250 spreads. Once the area of delamination is spread to one of the indicators devices 100, the electric circuit 130 of the respective indicator device 100 will break and the connected control monitoring system may trigger an alarm.

It should be noted that the term "comprising" does not exclude other elements or steps and the use of articles "a" or "an" does not exclude a plurality. Also elements described in association with different embodiments may be combined. It should also be noted that reference signs in the claims should not be construed as limiting the scope of the claims.

It should be noted that the term "attaching" may comprise bolting, riveting, welding or any other bonding of two materials, depending of the use of the materials and/or parts attached to each other. Where possible and useful, welding, bolting or riveting may be substituted by each other.

It is noted that it may also be possible in further refinements of the invention to combine features from different illustrative embodiments described herein. It should also be noted that reference signs in the claims should not be construed as limiting the scope of the claims.

In order to recapitulate the above described embodiments of the present invention one can state: The proposed invention may lead to an indicator device which is established in the laminates of e.g. the root of a wind turbine rotor blade. More specifically the indicator may be able to detect if layers of the composite material de-laminate.

The invention claimed is:

1. An indicator device for detecting a delamination of a composite material, including for detecting a delamination of a composite material of a wind turbine, or for detecting a delamination of a composite material of a wind turbine rotor blade, the indicator device comprising:

a first part arranged to fit into a hole in the composite material, wherein the hole spans at least a top layer and exposes a bottom layer of the composite material, and wherein when installed the first part is secured to the bottom layer, a second part arranged to fit into the hole, wherein when installed the second part is secured to the top layer, and an electric circuit that defines a loop in the hole, wherein the first part comprises at least a part of a lower part of the electric circuit, the second part comprises at least a part of an upper part of the electric circuit, and the lower part and the upper part are electrically connected to each other at a predetermined breaking point forming the electric circuit such that when the indicator device is in use in a composite material, if a delamination of the respective composite material occurs, the electric connection between the lower part and the upper part breaks at the predetermined breaking point, thus cutting the electric circuit.

2. The indicator device as set forth in claim 1, wherein the lower part of the electric circuit is fixed to a bottom part of the first part.

3. The indicator device as set forth in claim 1, wherein the upper part of the electric circuit is fixed inside the second part.

4. The indicator device as set forth in claim 1, wherein the second part comprises an electrical connection of the electric circuit, wherein the electrical connection is adapted for being connected to an external monitoring system.

5. The indicator device as set forth in claim 1, wherein the electric circuit acts a shunt.

6. The indicator device as set forth in claim 1, wherein when the indicator device is in use in the composite material, if a displacement of two layers of the respective monitored composite material relative to each other occurs, the electric connection between the lower part and the upper part breaks at the predetermined breaking point, thus cutting the electric circuit.

7. The indicator device as set forth in claim 6, wherein the displacement is caused by a shear stress in a parallel plane to a boundary plane between the respective two layers of the respective composite material.

8. The indicator device as set forth in claim 6, wherein the displacement is caused due at least a partial separation of the respective two layers of the respective composite material.

9. The indicator device as set forth in claim 6, wherein the electric connection between the lower part and the upper part breaks at the predetermined breaking point at a displacement of at least 1 mm.

10. A delamination detecting system for detecting a delamination of a composite material, including for detecting a delamination of a composite material of a wind turbine, or for detecting a delamination of a composite material of a wind turbine rotor blade, the delamination detecting system comprising:
the composite material, and
at least one indicator device according to claim 1, wherein
the composite material comprises the bottom layer and the top layer,
a lower part of each indicator device is fixed in the bottom layer,
an upper part of each indicator device is fixed on a surface of the top layer, and wherein
the surface of the top layer is facing away from the bottom layer.

11. The delamination detecting system as set forth in claim 10, the delamination detecting system comprising:
a plurality of said indicator devices, wherein the plurality of said indicator devices is arranged in the composite material in such a manner, that an area of delamination of the composite material may be localized.

12. A wind turbine rotor blade comprising a delamination detecting system of claim 10.

13. A wind turbine comprising a wind turbine rotor blade of claim 12.

14. A method for manufacturing a delamination detecting system, including a delamination detecting system for a wind turbine, or a delamination detecting system for a wind turbine rotor blade, the method comprising:
inserting at least one indicator device of claim 1 into a respective hole of the composite material,
fixedly arranging at least a part of a first part of each indicator device in a bottom layer of the composite material, and
fixedly arranging at least a part of a second part of each indicator device on a surface of a top layer of the composite material, wherein the surface is facing away from the bottom layer of the composite material.

15. The indicator device as set forth in claim 6, wherein the electric connection between the lower part and the upper part breaks at the predetermined breaking point at a displacement of at least 0.1 mm.

16. The method for manufacturing a delamination detecting system of claim 14, wherein fixedly arranging comprises gluing.

17. The indicator device as set forth in claim 1, the second part further comprising a cap that secures to a top surface of the top layer when the first part is installed in the hole such that the cap moves with the top surface of the top layer.

18. The indicator device as set forth in claim 1, wherein the indicator device is configured as a discrete insert that can be installed through the top layer.

* * * * *